United States Patent
Nowak

(10) Patent No.: US 9,581,666 B2
(45) Date of Patent: Feb. 28, 2017

(54) ARRANGEMENT TO GENERATE THE BASIC MAGNETIC FIELD AND A GRADIENT MAGNETIC FIELD OF A MAGNETIC RESONANCE TOMOGRAPHY SYSTEM, AND METHOD TO OPERATE A MAGNETIC RESONANCE TOMOGRAPHY SYSTEM

(71) Applicant: Stefan Nowak, Hessdorf (DE)

(72) Inventor: Stefan Nowak, Hessdorf (DE)

(73) Assignee: Siemens Aktiengesellschaft, Munich (DE)

( * ) Notice: Subject to any disclaimer, the term of this patent is extended or adjusted under 35 U.S.C. 154(b) by 636 days.

(21) Appl. No.: 14/090,107

(22) Filed: Nov. 26, 2013

(65) Prior Publication Data

US 2014/0145721 A1  May 29, 2014

(30) Foreign Application Priority Data

Nov. 29, 2012 (DE) .......................... 10 2012 221 918

(51) Int. Cl.
| | | |
|---|---|---|
| *G01R 33/381* | (2006.01) | |
| *G01R 33/385* | (2006.01) | |
| *G01R 33/44* | (2006.01) | |
| *H01F 7/20* | (2006.01) | |
| *A61B 5/055* | (2006.01) | |

(52) U.S. Cl.
CPC ............ *G01R 33/381* (2013.01); *A61B 5/055* (2013.01); *G01R 33/385* (2013.01); *G01R 33/445* (2013.01); *H01F 7/202* (2013.01)

(58) Field of Classification Search
CPC .. G01R 33/381; G01R 33/385; G01R 33/445; H01F 7/202; A61B 5/055
See application file for complete search history.

(56) References Cited

U.S. PATENT DOCUMENTS

| | | | | |
|---|---|---|---|---|
| 5,160,888 A | * | 11/1992 | Laukien ............. | G01R 33/3808 324/309 |
| 5,177,441 A | * | 1/1993 | Morich ................ | G01R 33/385 324/309 |
| 5,278,504 A | * | 1/1994 | Patrick ................. | G01R 33/385 324/318 |

(Continued)

FOREIGN PATENT DOCUMENTS

| | | |
|---|---|---|
| EP | 0709690 A1 | 5/1996 |
| WO | 2009124873 A1 | 10/2009 |

*Primary Examiner* — Rodney Bonnette
(74) *Attorney, Agent, or Firm* — Schiff Hardin LLP

(57) ABSTRACT

An arrangement to generate a basic magnetic field and a gradient magnetic field in a magnetic resonance tomography system include at least one basic electromagnet without an iron core that generates the basic magnetic field, at least three gradient field electromagnets that generate the gradient magnetic field, with the basic field electromagnet situated within the gradient field electromagnets such that during acquisition of magnetic resonance data from a subject, the basic field electromagnet is closer to the subject than the gradient field electromagnets. Because the basic electromagnet is situated within the gradient field electromagnets, an active shielding of the gradient field electromagnets can be foregone, and since the basic field electromagnet is situated near the subject, it can be a water-cooled air coil.

5 Claims, 1 Drawing Sheet

(56) References Cited

U.S. PATENT DOCUMENTS

| | | | |
|---|---|---|---|
| 2007/0216409 A1* | 9/2007 | Overweg | G01R 33/34046 324/262 |
| 2010/0056378 A1* | 3/2010 | Timinger | H01F 6/02 505/162 |
| 2010/0069738 A1* | 3/2010 | Timinger | G01R 33/288 600/410 |

* cited by examiner

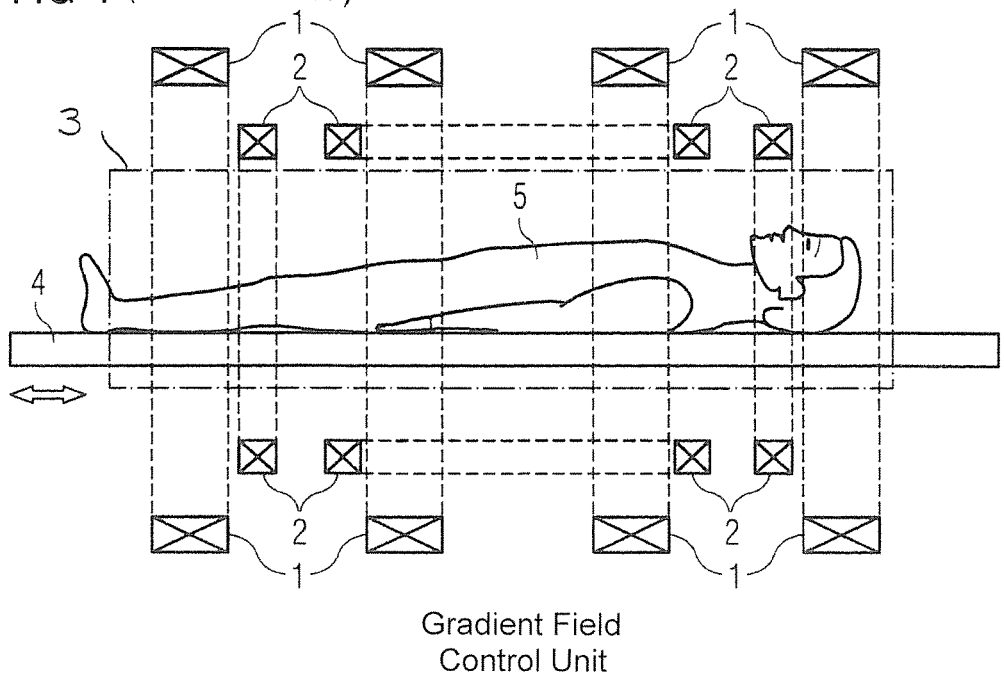
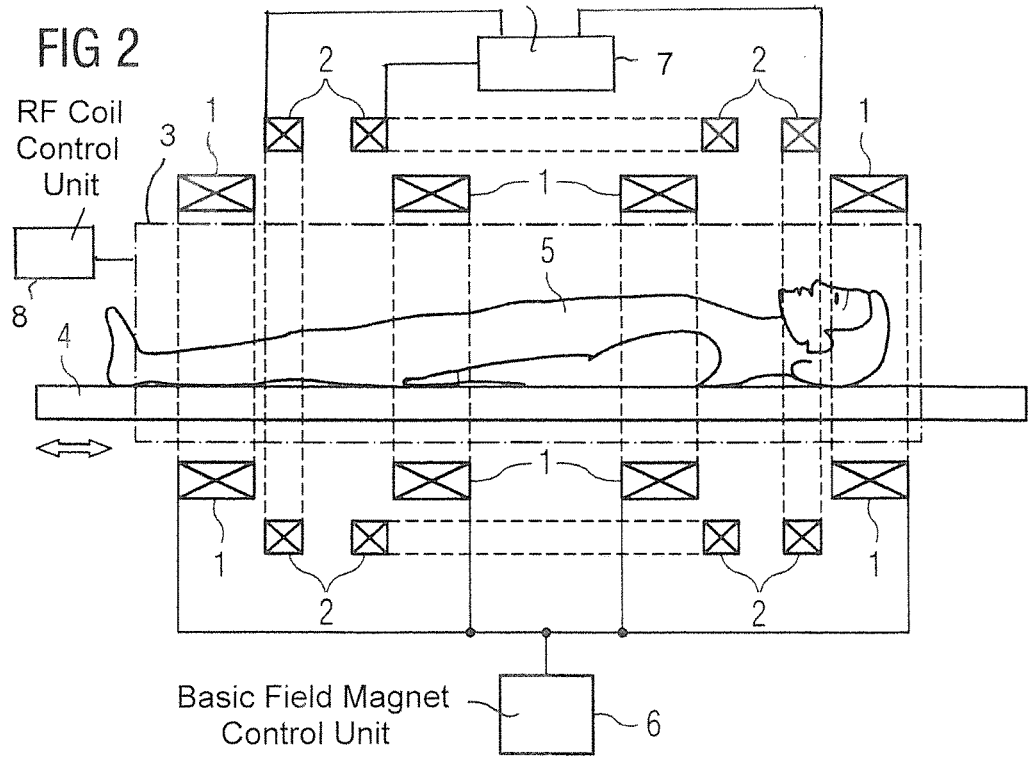

ARRANGEMENT TO GENERATE THE BASIC MAGNETIC FIELD AND A GRADIENT MAGNETIC FIELD OF A MAGNETIC RESONANCE TOMOGRAPHY SYSTEM, AND METHOD TO OPERATE A MAGNETIC RESONANCE TOMOGRAPHY SYSTEM

BACKGROUND OF THE INVENTION

Field of the Invention

The invention concerns an arrangement to generate the basic magnetic field and a gradient magnetic field of a magnetic resonance tomography system, a magnetic resonance tomography system with such an arrangement, and a method to operate a magnetic resonance tomography system with such an arrangement.

Description of the Prior Art

Magnetic resonance tomography (MRT) is a medical diagnostic method with the possibility to create slice images of the human body in arbitrary spatial orientations, the slice images showing selected anatomy without other anatomy superimposed thereon. Due to the high resolution and the high tissue contrast, a better depiction of the anatomical structures is achieved than with most other imaging methods. In particular, different soft tissue structures can be better differentiated.

In contrast to computed tomography (CT), x-rays are not used. Instead, the images are calculated from received electromagnetic signals that result from the interaction of hydrogen protons with a strong magnetic field. Hydrogen protons are very common in the human body. Conclusions about the chemical composition, the shape, the perfusion and pathological variations of the examined tissue can be obtained from the response of the hydrogen protons upon radiation of radio-frequency pulses (radio waves in the VHF range) and alternating magnetic fields.

An imaging magnetic resonance tomography system normally has four primary components:

A basic field magnet that generates a static, homogenous basic magnetic field across the measurement volume, so as to align or polarize nuclear spins in an examination subject situated in the measurement volume. Such magnets are executed as permanent magnets, electromagnets or as superconducting coils through which current flows. The direction of the stationary magnetic field is generally designated as the z-component in an orthogonal coordinate system. The other components are designated as x and y.

A radio-frequency transmission/reception device that generates a radio-frequency field in the examination subject so as to excite the aligned nuclear spins by suitable frequency selection. This device can likewise detect RF fields generated by the excited nuclear spins, as magnetic resonance signals (data).

A gradient coil system that is activatable to generate a magnetic field in a direction corresponding to that of the static magnetic field. The strength (amplitude) of the gradient magnetic field varies across the measurement volume. In the normal case, this change is a linear change along a spatial axis. The gradient coil system serves to generate magnetic gradient fields. The independent combination of three gradients that change in strength along three orthogonal spatial axes allows an arbitrary gradient direction to be set, as a combination of the gradient fields. A spatial encoding of the signal received with the radio-frequency transmission/reception device is implemented with the use of these gradients.

A central control unit that regulates the timing of the fields generated in a measurement (data acquisition sequence) and that processes the received signals.

Such a magnetic resonance tomography system is described as an example in DE 10 2008 018 265 A1.

In known magnetic resonance tomography systems, the complicated and expensive superconducting basic field coils and the permanently active basic magnetic field are disadvantageous.

SUMMARY OF THE INVENTION

An object of the invention is to provide an improved arrangement of the magnets for magnetic resonance tomography systems and an improved method to operate a magnetic resonance tomography system.

The underlying basis of the invention is to arrange electromagnets (also called resistive magnets) for the generation of the basic magnetic field within the gradient coil system, so that the basic field electromagnets are closer to the examination subject than are the gradient coils (gradient field electromagnets), and to fashion the electromagnets for generation of the basic magnetic field without an iron core (for example as a water-cooled copper coil). Moreover, the basic magnetic field is activated only upon execution of an imaging sequence.

The invention encompasses an arrangement to generate a basic magnetic field and a gradient magnetic field in a magnetic resonance tomography system. The arrangement has at least one basic electromagnet without an iron core with which the basic magnetic field is generated, and at least three gradient field electromagnets with which a gradient magnetic field is generated. The basic field electromagnet is arranged within the gradient field electromagnets such that the basic electromagnet is located nearer to the examination subject than the gradient field electromagnets, in the acquisition of magnetic resonance data from the examination subject. Because the basic electromagnet is situated within the gradient field electromagnets, an active shielding of the gradient field electromagnets can be foregone. Eddy currents cannot be excited in the "warm bore" of a superconducting magnet since such a structure is no longer present. A gradient field electromagnet that is not actively shielded operates significantly more efficiently than a shielded electromagnet. Since the basic field electromagnet is situated near the examination subject, for example on the patient, it can be executed as a water-cooled air coil, so the manufacturing and operating costs are reduced in comparison to superconducting electromagnets.

In an embodiment, the arrangement has a basic magnetic field generation unit that operates the basic field magnet so the basic magnetic field is generated only during execution of an image data acquisition sequence. The power loss in the basic electromagnet can thereby be reduced.

In a further embodiment, a stronger basic magnetic field can be generated only temporarily (for example for 5 seconds) by the basic magnetic field generation unit for the alignment of the nuclear spins in the examination subject, relative to a field strength of the basic magnetic field during the subsequent actual data acquisition portion of the overall imaging sequence. The signal-to-noise ratio is thereby improved in the reception of data. Audible noise development is also reduced due to a smaller action of forces between the electromagnets during the sequence run time.

In a development, the basic field electromagnet can be formed as an air coil.

In a preferred embodiment, the basic field electromagnet and the gradient field electromagnet can be fashioned as a jointly cast unit. Costs can thereby be avoided.

The invention also encompasses a magnetic resonance tomography system with an arrangement according to the invention as described above.

Furthermore, the invention encompasses a method to operate a magnetic resonance tomography system with an arrangement according to the invention as described above, wherein the basic magnetic field is generated only during the data acquisition portion of an image sequence.

In an embodiment of the method, the basic magnetic field is generated with a higher field strength only temporarily (for example for 5 seconds) for alignment of the nuclear spins in the examination subject relative to the strength of the basic magnet field during the subsequent data acquisition.

BRIEF DESCRIPTION OF THE DRAWINGS

FIG. 1 shows an arrangement for magnetic field generation in a magnetic resonance tomography system according to the prior art.

FIG. 2 shows an arrangement according to the invention for the generation of magnetic fields in a magnetic resonance tomography system.

DESCRIPTION OF THE PREFERRED EMBODIMENTS

FIG. 1 shows in cross-section an arrangement (in simplified presentation) of a magnetic resonance tomography system according to the prior art. The basic magnetic field is generated by the basic field electromagnet 1. Arranged within the basic field electromagnet 1 are the gradient field magnets 2. A patient 5 is located on a patient bed 4 that can be moved within the arrangement. A RF field is generated in the patient 5 with the use of a radio-frequency coil 3, that excites nuclear spins in the patient 5 by suitable frequency selection. The radio-frequency coil 3 can likewise receive the RF signals generated by the excited nuclear spins in the patient, as magnetic resonance signals (data).

FIG. 2 shows in cross-section an arrangement of a magnetic resonance tomography system according to the invention in a simplified presentation. In contrast to the arrangement presented in FIG. 1, the basic field electromagnets 1 that are air coils without an iron core, which are situated within a volume (amid the longitudinal extension of that volume) surrounded by the gradient field coils 2. Multiple gradient field coils 2, which form the gradient field electromagnets, are arranged outside the basic field electromagnets 1, thus spaced further from the patient 5 than the basic field electromagnets 1.

The air coils 1 generate the basic magnetic field and are energized or controlled by a basic magnetic field generation unit 6. Located within the air coils 1 is the radio-frequency coil 3. The air coils 1 and the gradient field coils 2 can be cast together and thus form a common unit. The patient 5 is located on a patient bed 4 that is arranged so as to be movable within the arrangement.

The gradient field coils 2 are operated by a gradient field control unit 7, and the RF coil 3 is operated by an RF coil control unit 8. The control units 6, 7 and 8 collectively operate the magnetic resonance data acquisition apparatus, formed by the aforementioned components, to execute a magnetic resonance imaging sequence that has a sequence duration, and that includes an image data acquisition portion, during which magnetic resonance image data are actually acquired (read out), that has a duration that is less than the overall duration of the imaging sequence.

According to the invention, the basic magnetic field is activated only during the execution of an image data acquisition sequence. The basic magnetic field is switched on and off with the maximum slew rate (rise rate) below the stimulation threshold for the patient. To align the nuclear spins in the patient, a higher basic magnetic field can be produced only temporarily (for between 1 and 10 seconds) than in the subsequent, actual image data acquisition portion of the overall imaging sequence.

It is advantageous to combine the basic electromagnets 1 with the z-gradient field coil 2.

Although modifications and changes may be suggested by those skilled in the art, it is the intention of the inventor to embody within the patent warranted hereon all changes and modifications as reasonably and properly come within the scope of his contribution to the art.

I claim as my invention:

1. A magnetic resonance apparatus comprising:
   at least one basic field electromagnet having no iron core;
   a basic field control unit configured to operate said at least one basic field electromagnet to generate a basic magnetic field;
   at least three gradient field electromagnets;
   a gradient field control unit configured to operate said at least three gradient field electromagnets to generate a gradient field;
   a radio-frequency (RF) coil;
   an RF control unit configured to operate said RF coil to generate an RF field;
   said basic field control unit, said gradient field control unit and said RF control unit being collectively configured to respectively operate said at least one basic field electromagnet, said at least three gradient field electromagnets and said RF coil to implement a magnetic resonance imaging sequence to acquire magnetic resonance data from an examination subject, said imaging sequence having a sequence duration and including a portion during which said magnetic resonance data are acquired from the examination subject, said portion having a duration that is less than said sequence duration;
   said at least one basic field electromagnet being situated within said at least three gradient field electromagnets, with said at least one basic field electromagnet being situated closer to the examination subject than said gradient field electromagnets during acquisition of said magnetic resonance data from the examination subject; and
   said basic field control unit being configured to operate said at least one basic field electromagnet in said magnetic resonance imaging sequence to generate said basic magnetic field with a higher field strength preceding said data portion of said magnetic resonance imaging sequence, to align nuclear spins in the subject, than a field strength of said basic magnetic field during said data acquisition portion.

2. The apparatus of claim 1 wherein said basic field electromagnet comprises an air coil.

3. The apparatus of claim 2 wherein said air coil is water-cooled.

4. The apparatus of claim 1 wherein said basic field electromagnet and said gradient field electromagnets are cast together as a unit.

5. A method to operate a magnetic resonance tomography apparatus comprising a basic field electromagnet situated within a plurality of gradient field electromagnets so that said basic field electromagnet is closer to an examination subject, during acquisition of magnetic resonance data from the subject, than are said gradient field electromagnets, and wherein said basic field electromagnetic has no iron core, said method comprising:

operating said gradient field electromagnets and said basic field electromagnet to execute an imaging sequence in which said magnetic resonance data are acquired from the subject, said sequence having a sequence duration and comprising a data acquisition portion, in which said magnetic resonance data are acquired, that has a duration that is less than said sequence duration;

operating said basic field electromagnet to generate said basic magnetic field only during execution of said sequence; and operating said basic field electromagnet to generate said basic magnetic field with a field strength that is higher preceding said data acquisition portion, to align nuclear spins in the examination subject, than a field strength of said basic magnetic field during said data acquisition portion.

* * * * *